US 6,739,195 B2
May 25, 2004

(54) SYSTEM AND METHOD FOR DETERMINING THE STATUS OF AN OBJECT BY INSONIFICATION

(75) Inventors: James A. Evans, Talluleh, LA (US); George L. Mason, Vicksburg, MS (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 52 days.

(21) Appl. No.: 10/118,001

(22) Filed: Apr. 9, 2002

(65) Prior Publication Data
US 2003/0188579 A1 Oct. 9, 2003

(51) Int. Cl.⁷ .............................................. G01N 29/18
(52) U.S. Cl. .............................. 73/598; 73/146; 73/660
(58) Field of Search ...................... 73/587, 593, 596, 73/597, 598, 660, 146.2, 146.3, 146.4, 146.5, 146; 310/334, 800; 340/443

(56) References Cited

U.S. PATENT DOCUMENTS

| | | | |
|---|---|---|---|
| 3,662,335 A | | 5/1972 | Fritze |
| 3,760,351 A | | 9/1973 | Thomas |
| 3,852,717 A | | 12/1974 | Hosaka |
| 4,150,567 A | | 4/1979 | Prevorsek |
| 4,233,838 A | | 11/1980 | Stiebel |
| 5,048,353 A | * | 9/1991 | Justus ..................... 73/862.55 |
| 5,067,347 A | | 11/1991 | Monch |
| 5,083,462 A | * | 1/1992 | Vermeiren et al. ............ 73/587 |
| 5,379,652 A | * | 1/1995 | Allonen ................... 73/862.55 |
| 5,677,488 A | * | 10/1997 | Monahan et al. ............. 73/593 |
| 5,781,104 A | | 7/1998 | Huang |
| 5,837,897 A | | 11/1998 | Jones |
| 5,889,464 A | | 3/1999 | Huang |
| 6,175,301 B1 | | 1/2001 | Piesinger |
| 6,175,302 B1 | | 1/2001 | Huang |
| 6,232,875 B1 | | 5/2001 | DeZorzi |

OTHER PUBLICATIONS

No Author Given, "Piezo Film Sensor Technical Manual," By Measurement Specialites, Inc. Part 1, pp. 2–8, Aug. 1998. And Part 6, pp. 2–8.

* cited by examiner

*Primary Examiner*—John E. Chapman
(74) *Attorney, Agent, or Firm*—Earl H. Baugher, Jr.

(57) ABSTRACT

A flexible piezoelectric-based transducer, mounted on a circumference of a rotating object senses acoustical energy traversing portions of the object. In a preferred embodiment, the transducer is affixed, using a suitable adhesive, within the enclosed portion of a wheel/tire assembly. The transducer senses acoustical energy, e.g., ultrasonic transmissions, generated by the tire contacting the road surface at its contact patch and, without need of external power, translates it to an electrical current and communicates it for further processing. Because the acoustical impedance of the tire casing changes with temperature, hot spots within the tire, as well as other characteristics of the tire's operation, can be detected. Further, any Doppler shift which occurs due to the rotating medium may be compensated for since the rate of tire rotation may be made known via a speed sensor. A position sensor may also be employed to indicate the position of the hot spot.

17 Claims, 3 Drawing Sheets

SYSTEM AND METHOD FOR DETERMINING THE STATUS OF AN OBJECT BY INSONIFICATION

STATEMENT OF GOVERNMENT INTEREST

Under paragraph 1(a) of Executive Order 10096, the conditions under which this invention was made entitle the Government of the United States, as represented by the Secretary of the Army, to the entire right, title and interest in any patent granted thereon by the United States. This and related patents are available for licensing. Please contact Bea Shahin at 217 373-7234 or Phillip Stewart at 601 634-4113.

BACKGROUND

A system using insonification senses acoustic energy to establish characteristics of a material. A preferred embodiment of the present invention uses a piezoelectric strip as an acoustical transducer to indicate the relative temperature of a tire while in use.

Modern tires are built using several layers (plies) of rubber and structurally enhancing material that may include embedded steel wire or mesh and synthetic cords or mesh in a strengthening belt that provides strength while maintaining resiliency. To insure adherence of the plies to each other during manufacture, the rubber must be at a specific temperature when joined to another layer. Additionally, the rubber, steel and synthetic material must adhere to each other, thus all material must be free of contaminants during the molding process.

If contaminants exist, or the curing process is compromised, the strengthening belt(s) will eventually separate from the rubber plies or individual plies of rubber will separate. This separation results in hot spots forming in the tire with eventual catastrophic failure of the tire. Inter-ply separation can result in complete destruction of the vehicle with loss of life. Thus, the ability to detect imminent tire failure may save lives and equipment.

This is particularly true in the case of airplane tires and automotive tires used at high speed. For example, excessive tire temperatures from tread separation and the like may result in catastrophic wheel well fires when aircraft tires are superheated and retracted into the aircraft. Of particular concern are truck tires used to carry heavy loads at higher inflation pressures than passenger car tires.

For heavy duty over-the-road trucks, tread separation can be problematic, especially when the truck involved is carrying hazardous materials. Many trucks use re-treaded or "recapped" tires, particularly on trailers, as an economy measure. Such tires are particularly prone to tread and ply separation.

Even if damage does not occur as a result of ply separation, the presence of shed truck treads, termed "gators," on the roadways presents a hazard to other motorists. Moreover, sudden blowouts of truck tires in the vicinity of passenger vehicles can be hazardous to the passengers. Unfortunately, there are no practical, yet economical, self-contained systems available to monitor and alert to heat build-up within tires. Available systems are expensive, bulky, or both, and many provide only localized information on temperature changes. Conventional tire testing systems generally deal with looking for defects (occlusions and the like) within tires for production testing purposes or are directed toward external measurements of temperature, tire pressure, and stress. Examples are represented in the following patents.

U.S. Pat. No. 5,837,897, Apparatus for Testing the Traction Properties of Pneumatic Tires, to Jones et al., Nov. 17, 1998, incorporated herein by reference, discloses an external ultrasonic device for tire testing which may be used to determine tire pressure.

U.S. Pat. No. 5,067,347, Method and Apparatus for Testing a Pneumatic Tire, to Mönch, Nov. 26, 1991, describes a method for testing a tire by pre-heating the air needed to inflate the tire to reduce the test period.

U.S. Pat. No. 4,233,838, Load Control for Tire Test Machine, to Stiebel, Nov. 18, 1980, describes an external controller for varying the load on a tire under test, that during equilibrium testing, correlates a relatively fast increase in temperature with a corresponding fast load increase to indicate incipient failure of the tire.

U.S. Pat. No. 4,150,567, Method of Estimating Energy Loss from Pneumatic Tires, to Prevorsek et al., Apr. 24, 1979, provides an equation for quantifying tire performance of two similar tires differing in only one characteristic by externally collecting selected temperature and heat generation rates, and determining dynamic tensile moduli from selected sections of the tires under varying conditions.

In addition to systems and methods for tire testing, there are patents for onboard systems, samples of which follow.

U.S. Pat. No. 3,852,717, Device for Automatically Detecting Abnormal Conditions in Vehicle Tires, to Hosaka et al., Dec. 3, 1974, provides a pressure switch and a thermistor mounted within a wheel assembly that are connected in series to a coupling unit, the primary coil of which is secured on the journal of the axle and the secondary coil of which is mounted concentrically on the vehicle's axle. A warning signal is sent to the driver when a threshold is exceeded.

U.S. Pat. No. 3,760,351, Apparatus and Process for Developing Electromagnetic Energy from Tire Flexure, to Thomas, Sep. 18, 1973, mounts within the tire one or more actuators that are reciprocated radially once each rotation of the tire by the normal distortion of the tire upon rotation. This action operates a generator, the energy derived therefrom usable for operating a separate device or for signaling tire operating parameters.

U.S. Pat. No. 3,662,335, Device for Road Vehicle for the Wireless Transmission of at Least One Measured Value of a Rotating Wheel to an Indicating Instrument, to Fritze, May 9, 1972, incorporated herein by reference, describes a wireless device for monitoring the performance of a tire while in operation. The internal wheel or internal tire bead-mounted coupling element, an oscillator-antenna with a resonant circuit, and a switch, extend coaxially to the vehicle hub, the elements themselves extending radially outside of the base of the wheel rim about the entire circumference of the wheel, being accommodated within or internally on the tire casing near an outer edge of the tire rim. The transmitter and associated antenna is mounted on the frame of the vehicle near the wheel for picking up the reflected signal from the wheel, with all signal processing electronics located on the vehicle and powered thereby.

More recently, designers have capitalized on the reduced size and expense of solid state electronics to effect an onboard solution, as evidenced in the following patents.

U.S. Pat. No. 6,232,875 B1, Apparatus and Method for Controlling a Tire Condition Module of a Vehicle Tire, to DeZorzi, May 15, 2001, describes onboard, i.e., internal to a tire/wheel assembly, multi-mode internally powered tire condition sensor/transmitter modules that include a motion sensor; an application specific integrated circuit (ASIC) that contains appropriate sensors, such as temperature and pressure sensors, and serves as the module's mode controller and signal processor; and an antenna providing output to effect a wireless link to a receiver module onboard the vehicle. Signals from the modules are received by the receiver module that contains appropriate circuitry for decoding the received signals and may contain an integrated controller for further processing and providing both a monitor status and an alert. The system specifically provides a "sleep" mode to conserve energy when the vehicle is stopped.

U.S. Pat. Nos. 6,175,302 B1, 5,889,464, and 5,781,104, each entitled Tire Pressure Indicator Including Pressure Gauges That Have a Self-Generating Power Capability, all to Huang, Jan. 16, 2001, Mar. 30, 1999, and Jul. 14, 1998, respectively, provide a set of pressure (only) gauges, each one to be installed in a tire/wheel assembly of a vehicle. The gauges communicate with a receiver onboard the vehicle. Each pressure gauge contains an internal power supply, a sensor, and a transmitter. For the '302 patent, the power supplying device is a self-generating voltage supply formed by a piezoelectric element, a spring, and a weight. The spring vibrates during wheel rotation, causing the piezoelectric element to generate energy for powering the gauge. The sensor includes a capacitor having a moving member sensitive to internal pressure, thus providing an indication of relative pressure via changes in capacitance. For the '464 patent, the sensor includes a sensing coil, a volume variable member, a magnetic core and an encoder. For the '104 patent the pressure sensor is a semiconductor and the unit further provides a rechargeable cell to be used with the piezoelectric element.

U.S. Pat. No. 6,175,301 B1, Low Tire Pressure Warning System, to Piesinger, Jan. 16, 2001, provides a low tire pressure warning module designed to be internally mounted in a tire/wheel assembly. Each module is powered by a small battery. An integrated pressure switch activates the battery and transmitter only when the pressure falls below a threshold value, transmitting a warning signal to a receiver onboard the vehicle.

Thus, an inexpensive and comprehensive method of measuring heat buildup in tires is needed for tire testing and development to assure designs are unlikely to separate during extremes of operation. Further, an inexpensive, yet reliable, system is needed as a vehicle on-board tire monitoring and alerting system.

SUMMARY

A non-intrusive detection and alerting system is used to monitor, detect, and alert to anomalies in the performance of rotating objects. A preferred embodiment continuously assesses temperature changes over the entire surface of a tire while in operation or under test. Additionally, methods of implementation are disclosed.

In a preferred embodiment of the present invention, a flexible piezoelectric strip or tape is mounted circumferentially on an inner circumference of a wheel so as to be concealed within the casing of a tire. This inner circumference is that central portion of the wheel from which the inner and outer rims of the wheel arise to grip the tire at its contact point with the wheel. This provides the piezoelectric strip sensory access to the contact surface of the tire at all times. The acoustic vibrations from the contact of the tire with the road surface, as transmitted to the wheel, provide the necessary excitation of the piezoelectric strip to permit it to generate a signal able to be communicated to a monitoring system.

The monitoring system may be one used in dynamic testing of the tire or a system onboard a vehicle for monitoring tire performance. A significant advantage is that no separate power source is required to be mounted on the wheel to effect the operation, i.e., the sensor system is "self-powered."

The sound of the tire contacting the road is directed from the external tire tread to the inside surface of the tire casing and across the pressurized air space within the tire cavity to the piezoelectric tape on the wheel. The acoustic pressure wave propagates across the inner cavity of the tire at a rate that is determined, at least in part, by the temperature of the medium in which it propagates. The acoustic energy thus transmitted excites the piezoelectric element within the tape. A measure of this energy, when compared to a reference standard, correlates to a measure of the instantaneous acoustical impedance of that portion of the tire tread that is contacting the road surface. Because a tire's acoustical impedance changes with temperature, hot spots within the tire may be detected in real time as changes in acoustical impedance. Certain other characteristics of the tire may be monitored also, such as the change in displacement of the tire outer surface as it comes in contact with the road.

The electric signal thus generated in the piezoelectric element from the acoustic energy may be provided to processors via a wireless or hardwire connection. The hardwire connection is made possible by a slip ring mounted on the wheel with conductors from the piezoelectric element fed through an air-tight channel in the wheel itself to an externally mounted slip ring on the wheel from whence the hard wire is attached to a processor. The signal may be amplified and converted at the slip ring to a suitable RF or optical wavelength for further transmission via a transmitter or used as is at the input to the processor where it may be modified as necessary. Alternatively, a transmitter, mounted externally on the wheel may convert the piezoelectric signal and transmit it via an antenna, fiber optic cable, or an inductive pickup to a processor that is part of an instrumentation package or onboard the vehicle as part of a monitoring system. The transmitter could operate at a suitable output power and RF frequency to meet applicable regulations or a simple inductive pickup could be provided as input to an onboard processor. The piezoelectric signal could be encoded to facilitate identification of the tire experiencing an anomaly. Alternatively, the system could include a fiber-optic link or the like for passing a signal converted to IR or other optical wavelengths.

An optional data source is a tire speed sensor, in any of a number of conventional configurations, that measures the rotation rate. At high rotation rates, i.e., those sufficient to induce the Doppler effect, any Doppler shift that occurs in the received signal may be used as a data source since the rotation rate would be known to the vehicle's onboard processor at any given time. The resultant Doppler shift may need to be sampled only once per each tire rotation, thus eliminating the need for high data sampling rates and sophisticated signal pickup devices and processors.

In one method of use, upon mounting a new type of tire on a wheel equipped with a preferred embodiment of the present invention, the system is calibrated. The predominant acoustic signals under normal operation at the factory recommended tire pressure are collected as a reference. As the tire heats to an operating temperature, the range of "normal" operation of that tire is ascertained and recorded for later use by an onboard processor. As the tire wears, the acoustic signal will change within a certain range. This range also may be provided to the processor so that normal tire wear is one attribute that is factored into the processor memory. The rotation rate of the tire is measured separately by a vehicle's onboard sensor and a real time comparison is made of the current acoustic signal to the stored acoustic signal expected for a good tire at that rotation rate and tire wear condition. If the phase difference for the current acoustic signal is outside the range of phase difference responses expected of a good tire, an alert signal is provided.

In a tire monitoring role, signals from a preferred embodiment of the present invention generate warnings of vehicle overloading or impending tire failure, e.g., due to tread separation or the presence of a foreign object. Increased temperature is a sign of tire overloading, severe under inflation, or other abnormal conditions. The operator is alerted to the danger of high temperatures and the alert may be used also to activate on-board tire inflation systems should low pressure be determined to be the cause.

Advantages of a preferred embodiment of the present invention include:

no separate power source requiring renewal of replacement;

low cost;

high reliability;

few parts with no interconnected moving parts;

easily retrofit to existing structures; and unsophisticated data processing and handling.

DETAILED DESCRIPTION

An inflated stationary tire's temperature is related to the pressure at which it is inflated. Once the tire rotates, there are three major frictional components that result in increased temperatures. These arise from:

tread contact with the road surface;

rotation of the tire that creates sidewall flex, i.e., the continuous expansion and contraction of the tire sidewall; and bearing friction in the wheel.

Figure 1:
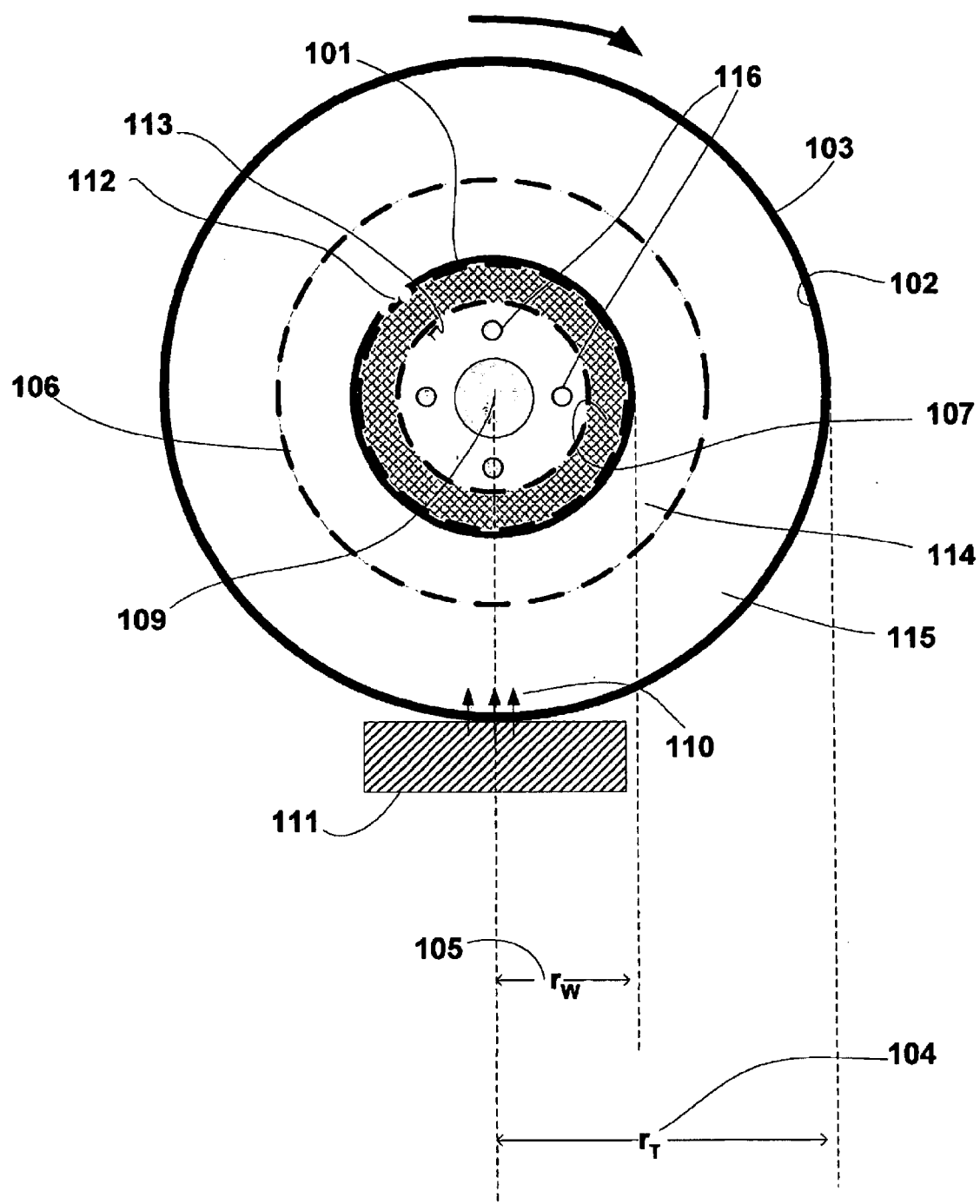
FIG. 1 is a side view of a preferred embodiment of the present invention taken of a vertical cut through the tire/wheel center.

Refer to FIG. 1. Hot spots in tires may be detected by collecting acoustical energy generated by the contact of the tire 115 at the "contact patch" with the road surface 111. A piezoelectric element, flexible so as to be embodied in a tape 101, is mounted to circumscribe the inner (covered) side of the inner diameter 107 of the wheel 114. If a hot spot occurs, a shift in the sound wave velocity will occur in the hot spot, due to the change of acoustical impedance of the tire casing 115 at the hot spot relative to a reference.

Sound is initiated at the outer perimeter 103 of the tire 115 as an acoustic pressure wave 110 generated by the tire's tread 102 contacting a surface 111. It could also, be initiated by a tuning fork (not separately shown) held under tension against the tire's surface 103 or a transducer (not separately shown) extended to the outside of the tire side wall 115. The sound wave 110 travels through the tire casing 115 itself, through the pressurized air in the cavity of the tire 115, to the inner surface 107 of the wheel 114. A piezoelectric tape 101 is affixed to the surface of the inner (enclosed) side 107 of a vehicle's wheel 114 farthest from the rims 106 of the wheel 114, prior to mounting the tire 115. This piezoelectric tape 101 is energized by this sound (acoustic wave) 110 impinging on the inner surface 107 of the wheel 114. The acoustical energy is converted to an electrical current (signal) by the piezoelectric tape 101. The piezoelectric tape 101 has electrical conductors (not separately shown) that are fed through an airtight seal 112 of the wheel 114 to a connector 113 suitable for allowing the signal generated by the piezoelectric tape 101 to be used by a device (not separately shown) for transmitting the signal to an amplifier 321 prior to processing by a processor 324 both of which may be incorporated in an onboard system 320.

The output of the piezoelectric tape 101 is analyzed using a phase determination algorithm. An acoustical pressure wave, f(x), is chosen such that:

$$f(x) = A\cos(\omega_1 t \pm \phi) \tag{1}$$

where:

A=the amplitude of the wave, $\omega_1 t$=the frequency of the wave, and $\phi$=the phase shift (assume a reference of 0° at ambient temperature)

The signal's velocity relation to frequency and wavelength is given by:

$$V = f\lambda \tag{2}$$

where:

$\lambda$=wavelength (m), f=frequency (Hz), and

V=wave velocity (m/s)

A high frequency component of the Fourier transform is selected form the general solution:

$$V(t) = a_v + \sum_{k=1}^{\infty} a_k \cos(k\omega_0 t) + b_k \sin(k\omega_0 t) \tag{3}$$

where:

$\omega_0 = 2\pi/T$, the fundamental radian frequency of the waveform,

T=the period of the waveform, and the coefficients $a_v$, $a_k$, and $b_k$ that describe the Fourier series components are given by:

$$a_v = \frac{1}{T}\int_0^T V dt \tag{4}$$

$$a_k = \frac{2}{T}\int_0^T a_k \cos(k\varpi t + \phi) dt \tag{5}$$

$$b_k = \frac{2}{T}\int_0^T B_k \sin(k\varpi t + \phi) dt, \text{ where } k = 1, 2, 3, \ldots \tag{6}$$

Any increase in temperature results in an increase in the wave velocity, given by:

$$V = (331.5 + 0.6 T_C) \tag{7}$$

where:

$T_C$ increase in temperature (° C.), and

V=velocity (m/s)

Since V changes with temperature, the wavelength, λ, also changes, Eqn. (2). The distance between the circumference of the wheel at the location the piezoelectric device is mounted and the inner circumference of the tire is given by:

$$d = r_t - r_w \quad (8)$$

where:
- $r_t$ = the circumference of the inner surface 102 of the tire, and
- $r_w$ = the circumference 107 of the part of the wheel 114 that is enclosed by the mounted tire 115 at the farthest point from the rim 106, i.e., where the piezoelectric tape 101 is affixed The function f(t) may be chosen such that:

$$\frac{d}{\lambda} < 1 \quad (9)$$

or for increased sensitivity $$\frac{d}{\lambda} \gg 1 \quad (10)$$

The increase in speed of the wave form at a given high value of f(t) results in a phase shift, φ. From Eqn. (7), this correlates to a temperature increase of:

$$T_C = \frac{V - 331.5}{0.6} \quad (11)$$

where:

$$V = \frac{\phi \lambda}{360} \quad (12)$$

Figure 2:
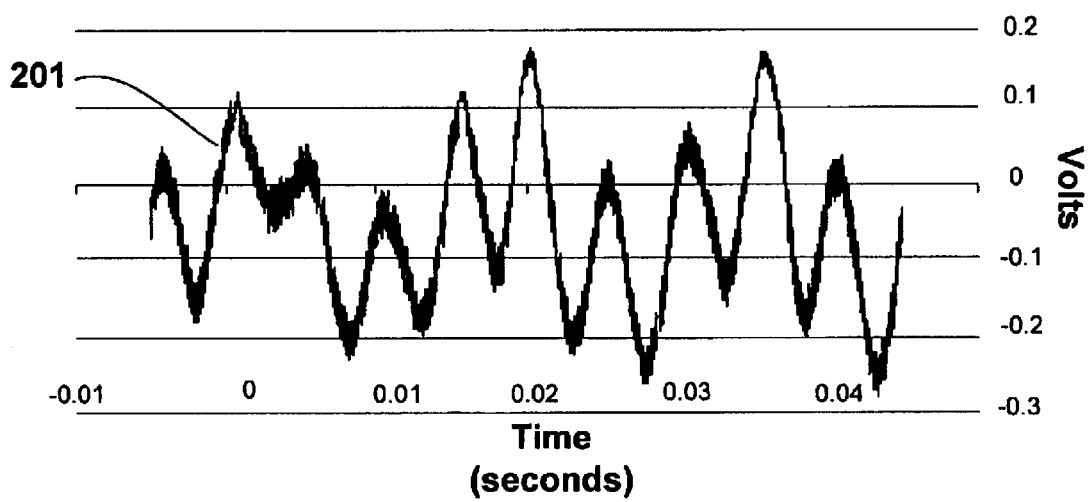
FIG. 2 is a representative analog signal response recorded at an audio frequency of 200 Hz for a tire inflated to 30 psi (cold).

Refer to FIG. 2 for a sample analog output signal 201. The output signal 201, recorded at the audio frequency of 200 Hz over a 0.05 sec interval of operation, represents a "normal" response of a tire inflated to 30 psi (cold). It is considered normal because of the absence of peaks representative of anomalous conditions. By correlating acoustical data to specific positions on the tire via a position sensor 312, it is possible to identify location of the hot spots within a tire, making subsequent investigation of a tire's failure more efficient. This is accomplished by establishing a time reference signature of a tire's characteristics and identifying the position of the abnormality by determining when the abnormality occurs relative to the reference.

EXAMPLE I

Test Device

A continuous strip of piezoelectric film 101 is affixed around the circumference 107 of the inner surface 107 of the wheel 114, thus providing a "pickup" sensor for acoustical energy generated by the tire 115 contacting a surface 111. In a preferred embodiment of the present invention, the piezoelectric tape 101 is a polarized fluoro-polymer, polyvinylidene fluoride (PVDF), marketed as DT4 by Measurements Specialties, Inc. A version of the tape is approximately 40 microns ($\mu$) (0.0016 in.) thick, 1.6 cm (0.64 in.) wide, and special ordered in a length approximating the circumference of the inner portion 107 of the wheel 114 that is enclosed by the mounted tire 115. See *Piezo Film Sensor Technical Manual, DT Series* Elements, Measurement Specialties, Inc., 2 pages, undated.

Figure 3:
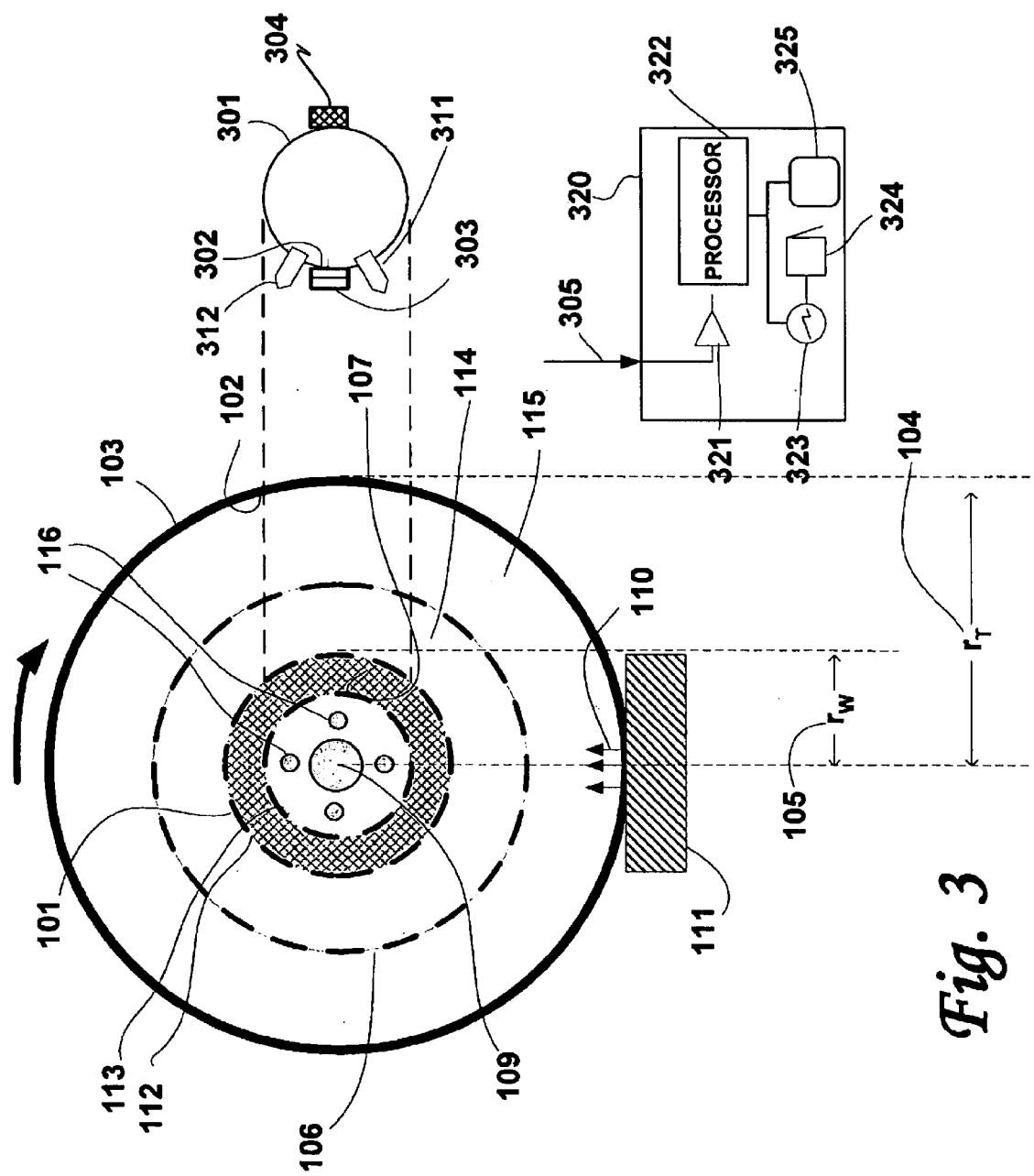
FIG. 3 includes the elements of FIG. 1 with the additional detail of components to be mounted on a slip ring on the external portion of the wheel.

Refer to FIG. 3. A slip ring 301, with suitable connector 302, on which a transceiver or relay module 303, optional battery (not separately shown) and the counter weight 304 are positioned is mounted on the outside of the wheel 114 as shown separately for clarity. As the tire 115 rotates over a surface 111, the transceiver or relay module 303 mounted on the slip ring 301 remains in the same position relative to the axle 109, made possible by using the counterweight 304 mounted on the slip ring 301 diametrically opposite the module 303.

This setup facilitates hardwired communication with separate test instrumentation (not separately shown) or an onboard monitoring system 320 while the tire 115 is rotating. During testing, the signal from two conductors (not separately shown) extending from the piezoelectric tape 101 is sent to a connector 113 through an airtight opening 112 in the wheel 114 to the connector 302 on the slip ring 301 where it is forwarded to test instrumentation via the transceiver or relay module 303. For certain types of testing, it is sufficient to collect the sensor data using instrumentation (not separately shown) that may be affixed to or may constitute the counterweight 304. For an onboard monitoring system 320, an amplifier 321 may be used to amplify the signal prior to processing in a processor 322. The output of the processor is sent to a display such as an indicator light 323, a buzzer or tone generator 324, or both.

The acoustic energy from tire contact may be available within a range of acoustic frequencies. Optimal frequencies are ultrasonic from 800–1200 KHz. Harmonics of sources, such as those emanating from the surface of the road or the interface between the tire and the surface, may be exploited also. A series of reference frequencies based on the tread patterns of the tire and rotation speed are established for the acoustic signal. The sensitivity of the phase shift, which establishes the relative amplitude of the temperature "spikes," is established at these reference frequencies. These reference values may be stored for comparison during testing or for use with a vehicle's onboard monitoring and alerting system(s).

EXAMPLE II

Onboard Safety Alert

Refer to FIG. 1. An inflated tire 115 is shown mounted on a wheel 114. The tire 115 is sealed to the wheel 114 at rims 106 and has an external tread surface 103 and an interior surface 102. The tire/wheel assembly is mounted on an axle 109 of a vehicle (not separately shown) using nuts on threaded studs (not separately shown) or bolts (not separately shown) engaging through holes 116 in the wheel 114.

An acoustic sensor in the form of piezoelectric tape 101 circumscribing the inner side 107 (enclosed by mounting the tire on the wheel) of the wheel's inner diameter is affixed via suitable adhesive. The piezoelectric tape 101 may be a polarized fluoro-polymer, polyvinylidene fluoride (PVDF), marketed as DT4 by Measurements Specialties, Inc. as described above. One version of DT4 is approximately 40$\mu$ (0.009 in.) thick, 2.2 cm (0.86 in.) wide, and special ordered in a length approximating the circumference of the inner portion 107 of the wheel 114. The piezoelectric tape 101 responds to changes in acoustics, e.g., those changes primarily generated from the excitation of the tire 115 as it contacts the surface 111. It produces a signal comprising an electrical current proportional to the instantaneous energy that is dissipated on it. This signal is transmitted to an amplifier 321 via any of a number of means known in the art.

Preferably the amplifier 321 is a high impedance amplifier (≧10 M Ω) at the front end of an onboard monitoring and alerting device 320.

The system may use existing processors 322 onboard a vehicle to translate the received acoustical signal 305 to enable an alert 323, 324 or display 325 relative temperature profiles of the tire 115. A set of equations as identified above may be implemented in the onboard processor 322, thus defining the phase shift for an instantaneous signal 305 well as for each of a series of reference frequencies, as necessary. An optional data source is a tire speed sensor 311, in any of a number of conventional configurations, which measures the rotation rate. At high rotation rates, i.e., those sufficient to induce the Doppler effect, any Doppler shift that occurs in the received signal 305 may be used as a data source since the rotation rate would be known to the vehicle's onboard processor 322 at any given time.

Upon mounting a new type of tire 115 on a wheel 114 equipped with a preferred embodiment of the present invention, the system is calibrated. The predominant acoustic signals 201 under normal operation at the factory recommended tire pressure are collected as a reference. As the tire 115 heats to an operating temperature, the range of normal operation of that tire 115 is ascertained and recorded for later use by the onboard processor 322. As the tire 115 wears, the acoustic signal 305 changes within a certain range. This range also may be provided to the processor 322 so that normal tire wear is one attribute that is factored into the processor's memory. The rotation rate of the tire 115 is measured separately by an onboard sensor 311 and a real time comparison is made of the current acoustic signal 305 to the stored acoustic signal 201 expected for a good tire 115 at that rotation rate and tire wear condition. If the phase difference for the current acoustic signal 305 is outside the range of base difference responses expected of a good tire 115, an alert 323, 324 is provided.

While the preferred embodiment of the present invention is directed toward temperature measurement, another embodiment of the present invention may measure other tire characteristics correlatable to acoustical impedance changes. For example, the formation of an inclusion, e.g., an air bubble or nail, is detectable by measuring sound propagating through the tire and its cavity. Further, while the present invention has been disclosed in the context of tire and vehicle testing, the availability of such real-time data could be used in modern day vehicle control systems to provide additional data inputs on parameters such as tire inflation, loading, speed calibration, and traction characteristics.

We claim:

1. A system for remotely sensing at least one characteristic of a round object incorporating a gas-filled enclosed portion while said object rotates upon a surface, said system comprising:

a flexible piezoelectric element incorporating at least one electrically conductive element to facilitate communication externally thereto, said flexible piezoelectric element receiving a physical input that is translated to an electrical output, wherein said flexible piezoelectric element substantially circumscribes an innermost circumference within said enclosed portion of said round object; and a device for receiving, processing and displaying said electrical output.

2. The system of claim 1 in which said round object is a tire having a side wall portion and a tread portion, said tire mounted on a wheel to establish said gas-filled enclosed portion, wherein said innermost circumference is the smallest circumference of said wheel established within said gas-filled portion.

3. A The system of claim 1 in which said flexible piezoelectric element comprises a polarized fluoro-polymer.

4. The system of claim 3 in which said polarized fluoro-polymer is polyvinylidene fluoride (PVDF).

5. The system of claim 4 in which said polyvinylidene fluoride (PVDF) is approximately 40 microns thick, 2.2 cm wide, and of a length approximating said innermost circumference.

6. The system of claim 1 in which said at least one electrically conductive element comprises two electrodes, said electrodes each incorporating connectors for facilitating external communications.

7. The system of claim 1 further comprising an amplifier in operable communication with said piezoelectric element and said device for receiving, processing and displaying said electrical output, said amplifier having an electrical impedance of at least approximately 10 mega ohms (M Ω).

8. A system for remotely detecting anomalies in at least one characteristic of a round object incorporating a gas-filled enclosed portion while said object rotates upon a surface, said system comprising:

a flexible piezoelectric element incorporating at least one electrically conductive element to facilitate communication externally thereto, said flexible piezoelectric element receiving a physical input that is translated to an electrical output, wherein said flexible piezoelectric element substantially circumscribes an innermost circumference within said enclosed portion of said round object;

at least one transceiver, external to said flexible piezoelectric element, in operable communication with said flexible piezoelectric element; and at least one processor in operable communication with said transceiver, wherein said processor determines and displays said anomalies in a pre-specified manner.

9. The system of claim 8 in which said round object is a tire having a side wall portion and a tread portion, said tire mounted on a wheel to establish said gas-filled enclosed portion.

10. The system of claim 8 in which said flexible piezoelectric element comprises a polarized fluoro-polymer.

11. The system of claim 10 in which said polarized fluoro-polymer is polyvinylidene fluoride (PVDF).

12. The system of claim 11 in which said polyvinylidene fluoride (PVDF) is approximately 40 microns thick, 2.2 cm wide, and of a length approximating said innermost circumference.

13. The system of claim 8 in which said at least one electrically conductive element comprises two electrodes, said electrodes each incorporating connectors for facilitating said external communication.

14. The system of claim 8 in which said transceiver incorporates an amplifier having an electrical impedance of at least approximately 10 mega ohms (M Ω).

15. A method for passively and remotely sensing and then actively determining and displaying indications of the occurrence of pre-specified characteristics of a round object incorporating a gas-flied annular section upon which said round object contacts a surface, the method comprising:

receiving at a flexible piezoelectric element circumscribing an innermost circumference circumscribed by said annular section energy generated at least in part at acoustic wavelengths, said energy traversing at least radially from the exterior of said annular section across at least said gas-filled portion of said annular section;

translating at least a portion of said received energy generated at acoustic wavelengths to an output as an electrical signal; and communicating said electrical signal to a device external to said piezoelectric element for subsequent processing, wherein said processing results in said determining and displaying of indications of the occurrence of said pre-specified characteristics.

16. A method for sensing pre-specified characteristics of a rotating object, the method comprising:

receiving at a flexible piezoelectric element circumscribing a circumference of said rotating object, acoustic energy traversing at least a portion of said object;

translating at least a portion of said received acoustic energy to a signal represented by an electrical current; and communicating said signal to a device external to said piezoelectric element for subsequent processing, wherein said processing results in identifying said pre-specified characteristics;

wherein said rotating object is a tire having a casing and a cavity, said circumference is that of the interior portion of a wheel on which said tire is mounted, and said portion of said tire in which said acoustic energy travels includes at least said casing and said cavity of said tire.

17. The method of claim 16 further comprising measuring angular position of pre-specified portions of said rotating object, wherein said processing further comprises correlating anomalies in said characteristics to said pre-specified portions.

* * * * *